(12) United States Patent
Resconi et al.

(10) Patent No.: US 6,391,991 B1
(45) Date of Patent: May 21, 2002

(54) PROCESS FOR THE PREPARATION OF AMORPHOUS POLYMERS OF PROPYLENE

(75) Inventors: Luigi Resconi; Fabrizio Piemontesi; Davide Balboni, all of Ferrara (IT)

(73) Assignee: Basell Technology Company BV, Hoofdorp (NL)

( * ) Notice: Subject to any disclaimer, the term of this patent is extended or adjusted under 35 U.S.C. 154(b) by 0 days.

(21) Appl. No.: 08/504,319

(22) Filed: Jul. 19, 1995

(30) Foreign Application Priority Data

Jul. 20, 1994 (IT) .......................... MI94A1517

(51) Int. Cl.$^7$ ................................. C08F 4/42
(52) U.S. Cl. ................ 526/160; 526/170; 526/127; 526/943; 526/134; 526/351; 526/348; 502/152
(58) Field of Search ................ 526/160, 943, 526/170, 127, 134, 351, 348; 502/152

(56) References Cited

U.S. PATENT DOCUMENTS

| | | | |
|---|---|---|---|
| 4,542,199 A | | 9/1985 | Kaminsky et al. |
| 4,931,417 A | | 6/1990 | Miya et al. |
| 5,491,207 A | * | 2/1996 | Hoel .......................... 526/129 |
| 5,594,080 A | * | 1/1997 | Waymouth et al. .......... 526/160 |

FOREIGN PATENT DOCUMENTS

| | | |
|---|---|---|
| EP | 0 283 739 A2 | 9/1988 |
| EP | 0 399 347 A2 | 11/1990 |
| EP | 0 575 875 A2 | 12/1993 |
| EP | 0 633 272 A1 | 1/1995 |
| WO | WO 92/00333 | 1/1992 |
| WO | WO 94/11406 | 5/1994 |

* cited by examiner

Primary Examiner—David W. Wu
Assistant Examiner—Ling-Siu Choi
(74) Attorney, Agent, or Firm—Bryan Cave LLP

(57) ABSTRACT

It is possible to prepare substantially amorphous polymers of propylene endowed with high molecular weights, operating at temperatures of industrial interest, by carrying out the polymerization reaction of propylene in the presence of metallocene catalysts comprising particular bis-indenyl or bis-4,5,6,7-tetrahydroindenyl compounds substituted in the 2-position on the indenyl or tetrahydroindenyl groups.

13 Claims, No Drawings

PROCESS FOR THE PREPARATION OF AMORPHOUS POLYMERS OF PROPYLENE

BACKGROUND OF THE INVENTION

1. Field of the Invention

The present invention relates to a process for the preparation of amorphous polymers of propylene.

The invention also relates to a process for the preparation of indene compounds suitable as metallocene ligands.

2. Description of the Prior Art

As it is well known, products of propylene homopolymerization can be either crystalline or amorphous. Whereas the polypropylene having isotactic or syndiotactic structure is crystalline, the polypropylene having essentially atactic structure appears to be amorphous. The atactic polypropylene, in the representation by the Fischer formula as described in "M. Farina, Topics Stereochem., 17, (1987), 1-111" shows methyl groups casually arranged from one or the other side of the polymeric chain. As described in the above mentioned publication, useful information on the structure can be obtained from N.M.R. analysis.

The amorphous polypropylene available on the market is mainly used in adhesive compositions and as additives for bitumens. Generally, it is a by-product of the isotactic polypropylene obtained in the presence of catalysts of the Ziegler-Natta type. The separation of small fractions of amorphous polypropylene from the remainder product however involves inconvenient separation processes with solvents.

More recently, in the polymerization reaction of olefins, catalysts based on metallocene compounds and alumoxane compounds have been used. Operating in the presence of these catalysts, polymers characterized by a narrow molecular weight distribution and endowed with structural characteristics of interest can be obtained.

In particular, by polymerizing propylene in the presence of metallocene catalysts, depending on the metallocene used crystalline or amorphous polypropylene can be obtained. However, the amorphous polypropylene obtainable in the presence of metallocene catalysts is generally endowed with low molecular weight.

U.S. Pat. No. 4,542,199 describes a catalytic system for the polymerization of olefins comprising a bis(cyclopentadienyl)zirconium and an alumoxane. From the polymerization reaction of propylene carried out in the presence of this catalyst, low molecular weight atactic polypropylene is obtained.

European patent application 283,739 describes a catalytic system for the polymerization of olefins comprising a partially substituted bis(cyclopentadienyl)zirconium and an alumoxane. From the polymerization reaction of propylene carried out in the presence of this catalyst, low molecular weight atactic polypropylene is obtained.

In U.S. Pat. No. 4,931,417, catalysts for the polymerization of olefins comprising a metallocene compound wherein two cyclopentadienyl rings are joined through a radical containing a silicon or germanium atom are described. The polymerization reaction of propylene carried out in the presence of these compounds partially substituted on the cyclopentadienyl rings gives rise to isotactic polypropylene, whereas with dimethylsilandiylbis(cyclopentadienyl) zirconium dichloride, low molecular weight atactic polypropylene is obtained.

In European patent application 399,347 a process for the polymerization of propylene in the presence of a catalyst comprising a metallocene having a cyclopentadienyl ring and a fluorenyl ring joined by a bridge, such as isopropylidene-(9-fluorenyl)(3-methylcyclopentadienyl) zirconium dichloride is described. An amorphous polypropylene is obtained, the structure of which however is not atactic, but is defined as syndioisoblocks. Namely, it is a structure wherein syndiotactic and atactic sequences alternate.

The international application WO 94/11406 describes a class of indenyl compounds substituted in the 2-position on the indenyl group. In the application it is stated that these compounds can be used as catalyst components for the polymerization of olefins. However, in the polymerization examples only homopolymers of ethylene and elastomeric copolymers of ethylene with propylene are prepared.

SUMMARY OF THE INVENTION

It has now been found that it is possible to prepare substantially amorphous polymers of propylene having high molecular weight, operating at temperatures of industrial interest, by carrying out the polymerization reaction of propylene in the presence of metallocene catalysts comprising particular bis-indenyl or bis-4,5,6,7-tetrahydroindenyl compounds substituted in the 2-position on the indenyl or tetrahydroindenyl groups.

Therefore, an object of the present invention consists of a process for the preparation of substantially amorphous polymers of propylene, comprising the polymerization reaction of propylene in the presence of a catalyst comprising the product of the reaction between:

(A) a metallocene compound selected from the bis-indenyl compounds of formula (I):

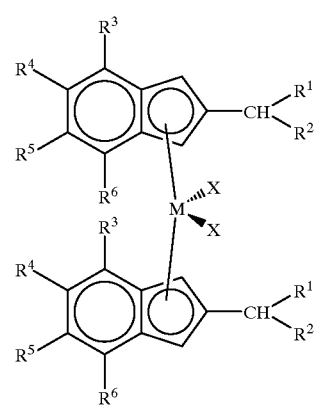

(I)

and the corresponding bis-4,5,6,7-tetrahydroindenyl compounds, wherein:

on each indenyl or tetrahydroindenyl group the substituents $R^1$ and $R^2$, same or different from each other, are hydrogen atoms, —$CHR_2$ groups or —CHR— groups form a cycle comprising from 3 to 8 carbon atoms, wherein the R substituents are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals or $C_7$–$C_{20}$ aralkyl radicals and can contain Si or Ge atoms;

the substituents $R^3$, $R^4$, $R^5$ and $R^6$, same or different from each other, are defined as R substituents, in addition two adjacent $R^3$, $R^4$, $R^5$ and $R^6$ substituents on the same ring can form a ring comprising from 5 to 8 carbon atoms; M is a transition metal atom of groups IVb, Vb or VIb of the Periodic Table;

substituents X, same or different from each other, are hydrogen atoms, halogen atoms, —$R^7$, —$OR^7$, —$SR^7$, —$NR^7_2$ or —$PR^7_2$ groups where substituent $R^7$ are defined as substituent R; optionally pre-reacted with an organometallic compound of aluminium of formula $AlR^8_3$ or $Al_2R^8_6$, wherein substituents $R^8$, same or different, are defined as substituent R or are halogen atoms; and (B) at least a compound selected from (a) the organometallic compounds of aluminum containing at least a heteroatom selected from oxygen nitrogen and sulphur, optionally in admixture with an organometallic compound of aluminum of formula $AlR^8_3$ or $Al_2R^8_6$, wherein substituents $R^8$, same or different, are defined as above, and (b) compounds capable of producing a metallocene alkyl cation.

Another object of the present invention is a process for the preparation of indene compounds of formula (VII):

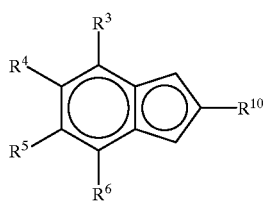

(VII)

suitable as metallocene ligands, which comprises the reaction of an aromatic compound of formula (VIII) with a compound of formula (IX), to obtain the indan-1-one of formula (X), wherein $R^3$, $R^4$, $R^5$ and $R^6$ have the above defined meaning, $R^{10}$ is a hydrogen atom or an alkyl radical $C_1$–$C_3$, Y is an halogen atom, according to the following reaction scheme:

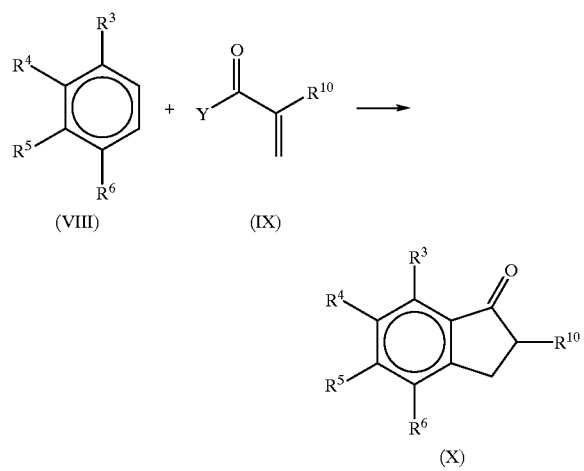

and the following conversion into the corresponding indene (VII).

DESCRIPTION OF THE PREFERRED EMBODIMENTS

Among the metallocene compounds of formula (I), preferred are those wherein, in each of the indenyl or tetrahydroindenyl groups the substituents $R^3$ are the same as substituents $R^6$, and substituents $R^4$ are the same as substituents $R^5$. More preferred are those in which all the substituents $R^3$ and $R^6$ are hydrogen atoms.

The transition metal M is preferably selected from titanium, zirconium, hafnium and vanadium, more preferably zirconium.

The substituents X are preferably chlorine atoms or a methyl radical.

Non limiting examples of metallocene compounds which can be used in the process of the present invention are:

bis(2-methyl-indenyl)zirconium dichloride,
bis(2,4,7-trimethyl-indenyl)zirconium dichloride,
bis(2,4,6-trimethyl-indenyl)zirconium dichloride,
bis(2,5,6-trimethyl-indenyl)zirconium dichloride,
bis(2,4,5,6,7-pentamethyl-indenyl)zirconium dichloride,
bis(2-ethyl-indenyl)zirconium dichloride,
bis(2-ethyl-4,7-dimethyl-indenyl)zirconium dichloride,
bis(2-ethyl-4,6-dimethyl-indenyl)zirconium dichloride,
bis(2-ethyl-5,6-dimethyl-indenyl)zirconium dichloride,
bis(2-ethyl-4,5,6,7-tetramethyl-indenyl)zirconium dichloride,
bis(2-propyl-indenyl)zirconium dichloride,
bis(2-propyl-4,7-dimethyl-indenyl)zirconium dichloride,
bis(2-propyl-4,6-dimethyl-indenyl)zirconium dichloride,
bis(2-propyl-5,6-dimethyl-indenyl)zirconium dichloride,
bis(2-propyl-4,5,6,7-tetramethyl-indenyl) zirconium dichloride,
bis(2-methyl-indenyl)zirconium dimethyl,
bis(2,4,7-trimethyl-indenyl)zirconium dimethyl,
bis(2,4,6-trimethyl-indenyl)zirconium dimethyl,
bis(2,5,6-trimethyl-indenyl)zirconium dimethyl,
bis(2,4,5,6,7-pentamethyl-indenyl)zirconium dimethyl, and the corresponding bis-4,5,6,7-tetrahydroindenyl compounds.

Alumoxanes usable in the catalyst of the invention are, for example, linear, cyclic or branched alumoxanes containing at least one group of the type (II):

(II)

where the substituents $R^9$, same or different from each other, are $R^1$ or a group —O—$Al(R^9)_2$, and optionally some $R^9$ may be halogen atoms.

In particular, alumoxanes of formula (III) may be used:

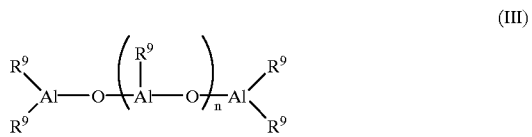

(III)

in the case of linear compounds where n is 0 or an integer of from 1 to 40 and the substituents $R^9$ are defined as substituents $R^1$, or alumoxanes of formula (IV):

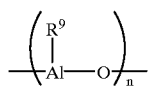
(IV)

in the case of cyclic compounds, with n which is an integer of from 2 to 40, and the substituents $R^9$ are defined as the substituents $R^1$.

Substituents $R^9$ are preferably methyl, ethyl, isobutyl.

Examples of alumoxanes suitable to be used according to the present invention are methylalumoxane (MAO) and isobutyl-alumoxane (TIBAO).

The alumoxanes used in the process of the present invention may be obtained by reaction between water and a organometallic compound of aluminum of formula $AlR^8_3$ or $Al_2R^8_6$, in which the substituents $R^8$, same or different from each other, are defined as above, with the condition that at least one $R^8$ is different from halogen. In that case these are made to react in a molar ratio of Al/water of from about 1:1 to 100:1.

Non limiting examples of the aluminum compound of formula $AlR^8_3$ or $Al_2R^8_6$ are:

$Al(Me)_3$, $Al(Et)_3$, $AlH(Et)_2$, $Al(iBu)_3$, $AlH(iBu)_2$, $Al(iHe)_3$, $Al(C_6H_5)_3$, $Al(CH_2C_6H_5)_3$, $Al(CH_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$, $Al_2(Et)_3Cl_3$, where Me=methyl, Et=ethyl, iBu=isobutyl, iHe=hexyl. Trimethyl aluminum (TMA) and triisobutyl aluminum (TIBAL) are preferred.

A particular class of organo-metallic compounds of aluminium minium used in the catalyst according to the invention are those obtainable by the reaction of water with the aluminum alkyl or alkylhydride in which at least one alkyl is not linear, in a molar ratio $Al/H_2O$ of from 1:1 to 100:1. Compounds of this type are described in the European patent application No. EP-575.875, the content of which is herein intended as incorporated in the present description.

Organo-metallic compounds of aluminum useable in the catalyst according to the invention are, in addition, those of formula (V):

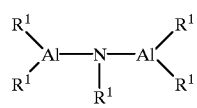
(V)

or of formula (VI):

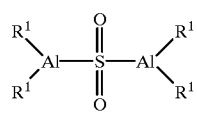
(VI)

where $R^1$ is defined as above.

The molar ratio between the aluminum and the metal of the metallocene compound is in general from about 10:1 to about 10000:1, and preferably from about 100:1 to about 5000:1.

Non limiting examples of the compound capable of forming alkyl metallocene cations are compounds of formula $Y^+Z^-$, where $Y^+$ is a Brönsted acid, capable of donating a proton and of irreversibly reacting with substituent $X^1$ or $X^2$ of the compound of formula (I) and $Z^-$ is a compatible anion, which does not coordinate, which is capable of stabilizing the active catalytic species which originates from the reaction of the two compounds, and is sufficiently labile in order to be removed by an olefinic substrate. Preferably the anion $Z^-$ comprises one or more boron atoms. More preferably the anion $Z^-$ is an anion of formula $BAr_4^{(-)}$, where the substituents Ar, same or different from each other, are aryl radicals such as phenyl, pentafluorophenyl, bis (trifluoromethyl)phenyl. Particularly preferred is the tetrakis-pentafluorophenyl-borate. In addition, compounds of formula $BAr_3$ may be conveniently used. compounds of this type are described, for example, in the published International patent application WO 92/00333, the content of which is incorporated in the present description.

The catalysts of the present invention may also be used on inert supports. That is what is obtained by depositing the metallocene compound (A), or the product of reaction of the latter with component (B), or component (B) and subsequently the metallocene compound (A), on an inert support such as, for example silica, alumina, styrene-divinylbenzene copolymer, polyethylene or polypropylene.

A particularly suitable class of inert supports used in the process of the present invention are porous organic supports functionalized with functional groups having active hydrogen atoms. Particularly preferred are those in which the organic support is a partially crosslinked styrene polymer. These supports are described in the European patent application EP-633,272, the content of which is incorporated in the present description.

The solid so obtained, in combination with further additions of the alkyl aluminum compound, either as such or pre-reacted with water, if necessary, is usefully used in gas phase polymerisation.

The metallocene compounds of formula (I) can be prepared by reaction of the corresponding. indenyl or tetrahydroindenyl ligands with a compound able to form a delocalized anion on the cyclopentadienyl ring, and then with a compound of formula $MX_4$, wherein M and the substituents X are defined as above.

In the case in which at least a substituent X of the metallocene compound of formula (I) to be prepared is different from a halogen, it is necessary to substitute at least a substituent X in the obtained metallocene with at least a substituent X different from halogen.

The reaction of substitution of substituents X with substituents X different from halogen is carried out with commonly known methods. For instance, when the desired substituents X are alkyl groups, the metallocenes can be allowed to react with alkylmagnesium halides (Grignard reactives) or with lithium alkyl compounds.

In the particularly advantageous process for the preparation of indene compounds of formula (VII):

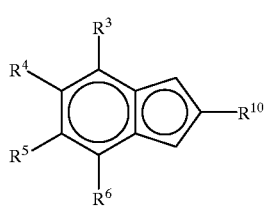
(VII)

according to the present invention, the indan-1-ones (X) can be converted in the corresponding indenes (VII) by different methods.

For instance, the indan-1-ones (X) can first be converted to the indan-1-oles and than dehydrated.

Reducing agents suitable for use in the reduction reaction are, for instance, lithium aluminum hydride and sodium boron hydride.

The dehydration reaction can be performed in the presence of an acid such as, for instance, p-toluen-sulphonic acid.

The propylene polymers obtainable with the process of the present invention are endowed with an atactic structure and, therefore, they are substantially amorphous. Their melting enthalpy ($\Delta H_f$) is generally not measurable.

The molecular weight of the above-described propylene polymers can even be very high. In fact the intrinsic viscosity can reach very high values, up to 10 dl/g and above.

The molecular weights of the propylene polymers, in addition to being high, are distributed over relatively limited ranges. An index of molecular weight distribution is represented by the ratio $M_w/M_n$ which is preferably less than 4, more preferably less than 3.

$^{13}$C-N.M.R. analysis gives information on the tacticity of the polymeric chain, that is the distribution of the relative configuration of the tertiary carbons.

The structure of the propylene polymer appears substantially atactic. Nevertheless, it is observed that the isotactic diads (m) appear to be more numerous than the syndiotactic diads (r). Namely, %(m)-%(r)>0, preferably %(m)-%(r)>5 and, more preferably %(m)-%(r)>10.

The Bernoullianity index (B), defined as:

$$B=4 [mm][rr]/[mr]^2$$

has values near unity, generally in the range 0.7–1.3, preferably in the range 0.8–1.2.

In the process of the invention, the polymerization reaction of propylene can be carried out in the presence of one or more olefins selected from ethylene and the α-olefins containing from 4 to 20 carbon atoms. Non limitative examples of these α-olefins are 1-butene, 1-pentene, 1-hexene, 1-octene and 1,5-hexadiene.

In particular, with the process of the present invention it is possible to prepare substantially amorphous copolymers of propylene with small quantities, that is up to about 10% by mole, of comonomeric units.

The possibility of obtaining directly, as the only product of the polymerization reaction of propylene, a substantially amorphous polypropylene endowed with high molecular weight is an advantage over the traditional processes.

The process of the polymerization of olefins according to the invention may be carried out in liquid phase, optionally in the presence of an inert hydrocarbon solvent, or in gas phase. The hydrocarbon solvent. may be aromatic such as toluene, or aliphatic, such as propane, hexane, heptane, isobutane, and cyclohexane.

The polymerization temperature is generally from −100° C. to +80° C., and more preferably from −50° C. to +50° C. The lower the polymerization temperature, the higher the molecular weight of the polymer obtained results.

In particular, by the process of the invention propylene polymers may be obtained having molecular weights of industrial interest at relatively high temperatures. The molecular weight of the polymers obtained in the presence of the catalysts of the invention are in any case higher with respect to those polymers obtained with the corresponding catalysts in which the indenyl group of the metallocene compound is not substituted in the 2-position.

The molecular weight of the polymer may be in addition varied, by varying the type or concentration of the catalytic components or by using molecular weight regulators such as, for example, hydrogen.

The molecular weight distribution may be varied by using mixtures of different metallocenes, or by carrying out the polymerization in more steps which differ in the polymerization temperature and/or the concentration of the molecular weight regulator.

The polymerization yield depends on the purity of the metallocene component of the catalyst. Moreover the metallocene compound obtained by the process of the invention may be used as such or may undergo purification treatment.

The different catalyst components may be put into contact before the polymerization. The contact time is generally from 1 to 60 minutes, preferably from 5 to 20 minutes. The concentration of the pre-contact for the metallocene component (A) are from $10^{-2}$ to $10^{-8}$ mol/l, while for component (B) are from 10 to $10^{-3}$ mol/l. The precontact is generally carried out in the presence of a hydrocarbon solvent and, optionally, small quantities of monomer.

The following examples are given to illustrate the invention and not to limit it.

Characterisations

The intrinsic viscosity [η] is measured in tetraline at 135° C.

The Differential Scanning Calorimetry (DSC) have been carried out on a DSC-7 instrument by Perkin Elmer Co. Ltd. according to the following process. Approximately 10 mg of sample is heated to 180° C., with a scanning speed equal to 1–0° C./minute. The sample is maintained at 180° C. for 5 minutes and then cooled at a scanning speed equal to 10° C./minute. Then a second scanning is carried out in the same way as the first. The values reported are those from the second scanning.

The $^{13}$C-N.M.R. analysis of the polymer have been carried out on Bruker AC200 instrument at 50.323 MHz, using $C_2D_2Cl_4$ as solvent (about 300 mg of dissolved polymer in 2.5 ml of solvent), at a temperature of 120° C.

The $^1$H-N.M.R. analysis of the polymer have been carried out on a Bruker AC200 instrument at 200.133 MHz, using $CDCl_3$ as solvent at room temperature.

The gas-cromatographic analysis (GC) have been carried out with a Hewlett-Packard Gas Cromatograph (5890 Series II) with a HP5 column (5% phenyl methyl silicon) of 50 meters, 0.22 i.d., film thickness 0.5 μm. It has been worked in a temperature range of from 30 to 300° C., with a gradient of 4° C./minute, with an initial isotherm of 4 minutes. The injector was on the column (1 μl of sample dissolved in THF or $CH_2Cl_2$).

Preparation of the Metallocenes

All the operations have been carried out under an inert atmosphere.
THF=tetrahydrofuran
Et$_2$O=diethyl ether

EXAMPLE 1

Bis(2-methyl-indenyl)zirconium Dichloride (a) Synthesis of 2-methyl-2-indanol

A solution of 36 g of 2-indanone (distilled before use) in 400 ml of anhydrous Et$_2$O was slowly added to a mixture of methyl magnesium bromide (100 ml of a 3M solution in hexane) in 200 ml of Et$_2$O at 0° C.

The mixture was stirred at room temperature. After 3 hours the reaction was stopped with 350 g of ice and a solution of 30 g of $NH_4Cl$ in 500 ml of water. The organic layer was separated, washed with 500 ml of a saturated solution of $NaHCO_3$ and then 500 ml of water, dried on sodium sulphate and concentrated under vacuo.

37.8 g of a clear yellow solid was obtained identified as 2-methyl-2-indanol by N.M.R. and GC-MS analysis.

(b) Synthesis of 2-methyl-indene 1 g of p-toluene-sulphonic acid monohydrate and 25 g of the product obtained at point (a) were dissolved in 100 ml of toluene. The solution obtained was maintained under reflux for 2 hours. GC analysis of the reaction crude indicated at this point that the conversion to 2-methyl-indene was 96%. The solution was concentrated under vacuo and then distilled in the presence of a small amount of 4-t-butyl-catechol and of 2 drops of NaOH. 16.7 g of 2-methyl-indene was obtained having boiling point of 58–60° C. at 2 mm Hg.

$^1$H-N.M.R. ($CDCl_3$), δ (ppm): 7.4–7.0 (m, 4 H), 6.11 (s, 1 H), 3.21 (s, 2 H), 2.10 (s, 3 H).

(c) Synthesis of bis(2-methyl-indenyl)zirconium dichloride 4.4 ml of a solution 2.5M of n-butyllithium in hexane were added to a solution of 1.42 g of 2-methyl-indene obtained at point (b), dissolved in 30 ml of THF at 0° C. After the addition the solution was left to return to room temperature and maintained under stirring for a further 4 hours. The volatile substances were removed under vacuo and the solid so obtained was washed with pentane.

1.27 g of $ZrCl_4$ in powder form was added to this solid and the whole was suspended in pentane. In order to facilitate the reaction, 1 ml of THF was added. The suspension was maintained under stirring overnight and at the end the solid was separated by filtration and washed with pentane.

The product so obtained was dissolved in $CH_2Cl_2$, filtered, and the solution dried. 1.51 g of a yellow powder was so obtained identified as bis(2-methyl-indenyl) zirconium dichloride from its $^1$H-N.M.R. spectrum.

$^1$H-N.M.R. ($CDCl_3$), δ (ppm): 7.75–7.55 (m, 4 H, Ar), 7.35–7.15 (m, 4H, Ar), 5.81 (s, 4 H, H1 e H3), 2.04 (s, 6 H, Me).

EXAMPLE 2
(Comparison)

Bis(indenyl)zirconium Dichloride 7.0 ml (60 mmols) of indene were dissolved in 20 ml of anhydrous THF, the solution was cooled to −78° C. and treated with 40.0 ml of n-butyllithium (1.5 M in hexane, 60 mmols). It was left to warm to room temperature thus obtaining a red colored solution.

In a 100 ml round-bottomed flask provided with reflux cooler, 7 g of $ZrCl_4$ (30 mmols) were cooled to −78° C. and treated with 30 ml of THF (exothermic reaction). Thereafter, the whole was heated under reflux for 30 minutes, until a clear, brown coloured solution was obtained.

The solution of indenyl lithium was added, at room temperature, to the solution of the $ZrCl_4$/THF adduct. It was kept stirred for 2 hours (a yellow suspension was formed) and thereafter the solvent was completely evaporated.

The residue was suspended in $Et_2O$ filtered off, washed repeatedly with $Et_2O$ and extracted with dichloromethane. The solution was dried and the product was washed with $Et_2O$ and then with pentane: 4.35 g of bis(indenyl)zirconium dichloride were thus obtained (36.8%).

EXAMPLE 3

Bis(2,4,7-trimethyl-indenyl)zirconium Dichloride

(a) Synthesis of 2,4,7-trimethyl-indan-1-one 80 mL of $CH_2Cl_2$ and 19 g of $AlCl_3$ (Aldrich) were placed in a 250 mL, 3-neck round bottomed flask equipped with magnetic stirring bar, 100 mL dropping funnel, thermometer and reflux condenser. The flask was placed in a Dewar and cooled to 0° C. A solution of 7.7 mL of metacryloyl chloride (Aldrich, 90%) and 8.7 mL of p-xylene (Aldrich) in 50 mL of $CH_2Cl_2$ was placed in the dropping funnel and added dropwise to the stirred $AlCl_3$/$CH_2Cl_2$ slurry over 2 hours at 0° C. A red slurry was obtained, which was allowed to warm to room temperature and stirred overnight (18 hours). The slurry was then poured into a flask containing 100 mL of 37% HCl and 100 g of ice. The solids were decanted off, the organic layer separated, the aqueous layer extracted with $Et_2O$ (3×100 mL). The combined organic layers were washed with a saturated aqueous solution of $NaHCO_3$ and then water, dried over $Na_2SO_4$, filtered and evaporated to leave 12.75 g of a yellow-orange oil, containing 54% 2,4,7-trimethyl-indan-1-one and 19.9 % dimers (GC). Yield based on GC purity 56%. This product was used without any further purification.

(b) Synthesis of 2,4,7-trimethyl-indan-1-ol 2.7 g of $LiAlH_4$ and 250 mL $Et_2O$ were placed in a 3-neck 500 mL round bottomed flask equipped with magnetic stirring bar, reflux condenser and 100 mL dropping funnel. A 100 mL solution of 12.73 g of the product obtained at point (a) in $Et_2O$ was placed in the dropping funnel and added dropwise at room temperature over 1 hour in the stirred $LiAlH_4$/$Et_2O$ slurry. At the end of the addition, the slurry was refluxed for two hours, then cooled with an ice water bath. Subsequently, 5 mL of $H_2O$, 5 mL of a 10% NaOH solution and again 5 mL of $H_2O$ were slowly added, the slurry was filtered and the filtrate dried over $Na_2SO_4$, filtered and evaporated on the rotavac to leave 12.053 g of a straw-yellow oil. GC analysis shows the presence of the two diastereomers of 2,4,7-trimethyl-indan-1-ol (38.5% and 20.1%).

(c) Synthesis of 2,4,7-trimethyl-indene 12.0 g of the product obtained at point (b), 75 mg of p-toluen-sulfonic acid and 150 mL of toluene were placed in a 250 mL round bottomed flask equipped with magnetic stirring bar. The solution was heated to 80° C. for 15 minutes, then treated with a saturated $NaHCO_3$ aqueous solution. The organic layer was separated, washed with water, dried over $Na_2SO_4$ and evaporated in vacuo to leave 8.68 g of an orange oil. This oil was vacuo-distilled to yield 4.5 g of a straw-yellow solid. GC analysis: 2,4,7-trimethylindene 92.4%.

$^1$H-N.M.R. ($CDCl_3$), δ (ppm): 6.97 (d, J=7.6 Hz, 1 H, Ar), 6.84 (d, J=7.6 Hz, 1 H, Ar), 6.62–6.58 (m, 1 H, H3), 3.20 (bs, 2 H, H1), 2.37 (s, 3 H, Me), 2.30 (s, 3 H, Me), 2.19 (s, 3 H, Me2?).

This product was used without any further purification.

(d) Synthesis of bis(2,4,7-trimethyl-indenyl) zirconium dichloride

A solution of 4.0 g of the 2,4,7-trimethylindene obtained at point (c) in 20 ml THF was added dropwise to a suspension of 1.04 g KH in 80 ml THF at room temperature. H$_2$ evolution was observed. At the end of the addition the mixture was stirred until gas evolution ceased (2 hours). The remaining solid was decanted off and the dark brown liquid was transferred into a 100 ml dropping funnel and added dropwise into a flask containing a rapidly stirring solution of 4.4 g of ZrCl$_4$(THF)$_2$ in 50 ml THF. During the addition a green-yellow suspension was obtained. After stirring at room temperature for 2 hours (yellow suspension) the volume of the slurry was concentrated to 10 ml and an equal volume of Et$_2$O was added. The mixture was stirred for a few minutes and filtered. The filtrate was cooled to −20° C. for 2 days, and 1.10 g of solid precipitated and were isolated by filtration (A). The yellow solid was washed with 5 mL HCl 4N, 5 mL H$_2$O, 5 mL EtOh and 2×5 mL Et$_2$O. After drying, 1.48 g of a bright yellow solid were obtained (B). The two solid fractions (A) and (B) were combined and continuously extracted with CH$_2$Cl$_2$ (80 mL, 2 hours), then dried, yielding 2.02 g of (2,4,7-trimethyl-indenyl)$_2$ZrCl$_2$ pure by $^1$H-N.M.R. (yield 35%).

$^1$H-N.M.R. (CDCl$_3$), δ (ppm): 6.86 (s, 4 H, H5 e H6), 6.36 (s, 4 H, H1 e H3), 2.44 (s, 12 H, Me4 eMe7), 2.14 (s, 6 H, Me2).

EXAMPLE 4
(Comparison)

Bis(4,7-dimethyl-indenyl)zirconium Dichloride (a) Synthesis of 4,7-dimethyl-indan-1-one 180 mL CH$_2$Cl$_2$ and 36 g anhydrous AlCl$_3$ (Carlo Erba) were charged in a 3-neck 0.5-L round bottomed flask equipped with magnetic stirring bar, 250-ml dropping funnel, thermometer and reflux condenser. A solution containing 31 ml p-xylene and 21 ml acryloylchloride (Aldrich) in 100 ml CH$_2$Cl$_2$ was placed in the dropping funnel. This solution was added dropwise over 4 hours to the flask, the content of which was kept under stirring at the temperature of 0° C. with a bath of water and ice. Evolution of HCl was observed and the reaction mixture turned dark brick-red. After addition was complete, the mixture was allowed to warm to room temperature and stirring was continued overnight (18 hours). The reaction mixture was poured in a flask containing 250 g ice and 250 ml HCl 37%, the organic phase was separated and the acqueous phase was extracted with Et$_2$O (3 times). All organic fractions were combined and washed with saturated aqueous NaHCO$_3$ and water, dried with Na$_2$SO$_4$, filtered and the solvent was removed in vacuo. 38.25 g of light yellow-orange oil were obtained. This product was used without any further purification.

(b) Synthesis of 4,7-dimethyl-indan-1-ol 3.0 g of LiAlH$_4$ and 300 ml anhydrous THF were placed in a 3-neck 1 liter round bottomed flask equipped with magnetic stirring bar, 250 mL dropping funnel and reflux condenser. A 250 mL solution of 38.25 g of the product obtained at point (a) in THF was placed in the dropping funnel. This solution was added dropwise at room temperature over 1 hour to the flask the content of which was kept under stirring. At the end of the addition, the slurry was refluxed for 1.5 hours, then cooled with an ice water bath. Subsequently, 10 mL of H$_2$O, 10 mL of a 15% NaOH solution and again 10 mL of H$_2$O were slowly added. The obtained slurry was filtered and the filtrate dried over Na$_2$SO$_4$, then filtered and evaporated to leave 40.16 g of a dark-red oil.

(c) Synthesis of 4,7-dimethyl-indene

All the product obtained at point (b), 350 mg of p-toluensulfonic acid and 400 mL of benzene were placed in a 3-neck 500 mL round bottomed flask equipped with magnetic stirring bar and of a device for azeotropes collection. The obtained solution was heated for 15 minutes up to benzene reflux, then treated with a saturated NaHCO$_3$ aqueous solution. The organic layer was separated, washed with water, dried over Na$_2$SO$_4$, filtered and evaporated in vacuo to leave 28.854 g of a viscous dark-brown oil. This oil was vacuo-distilled to yield 12.3 ml of a clear colorless liquid, identified as 4,7-dimethylindene by its $^1$H-N.M.R. spectrum.

(d) Synthesis of bis(4,7-dimethyl-indenyl)zirconium dichloride

A solution of 5.8 g of 4,7-dimethylindene obtained at point (c) in 30 ml THF was added dropwise to a suspension of 1.8 g KH in 90 ml THF at room temperature. H$_2$ evolution was observed. At the end of the addition the mixture was stirred until gas evolution ceased (1.5 hours). The remaining solid was decanted off and the green-brown liquid was transferred into a 250 ml dropping funnel and added dropwise into a flask containing a rapidly stirring solution of 7.12 g of ZrCl$_4$(THF)$_2$ in 55 ml THF. During the addition the formation of a bulky yellow precipitate was observed. Additional 80 ml of THF were added to facilitate stirring. After stirring at room temperature for 2 hours, the volume of the suspension was concentrated to 60 ml and an equal volume of Et$_2$O was added. The mixture was stirred for a few minutes and filtered. The yellow solid was continuously extracted with CH$_2$Cl$_2$ for 20 hours, then dried, yielding 7.15 g of a lemon-yellow solid identified as bis(2,4,7-trimethyl-indenyl)zirconium dichloride by its $^1$H-N.M.R. spectrum.

$^1$H-N.M.R. (CDCl$_3$), δ (ppm): 6.96 (s, 4 H, H5 e H6), 6.48 (t, J=3.4 Hz, 2 H, H2), 6.24 (d, J=3.4, 4 H, H1 e H3) 2.43 (s, 12 H, Me).

EXAMPLE 5

Bis(2.4,6-trimethyl-indenyl)zirconium Dichloride (a) Synthesis of 2,5,7-trimethyl-indan-1-one 160 mL of CH$_2$Cl$_2$ and 38 g of AlCl$_3$ (Aldrich) were placed in a 500 mL, 3-neck round bottomed flask equipped with magnetic stirring bar, 250 mL dropping funnel, thermometer and reflux condenser. The mixture was cooled to 0° C. A solution of 15.4 mL of metacryloyl chloride (Aldrich, 90%) and 17.4 mL of m-xylene (Aldrich) in 100 mL of CH$_2$Cl$_2$ was placed in the dropping funnel and added dropwise to the stirred AlCl$_3$/CH$_2$Cl$_2$ slurry over 2 hours at 0° C. A red slurry was obtained, which was allowed to warm to room temperature and stirred overnight (18 hours). The slurry was then poured into a flask containing 200 mL of 37% HCl and 200 g of ice. The solids were decanted off, the organic layer separated, the aqueous layer extracted three times with Et$_2$O. The combined organic layers were washed with a saturated aqueous solution of NaHCO$_3$ and then water, dried over Na$_2$SO$_4$, filtered and evaporated to leave 26.13 g of dark green liquid, containing 83.2% 2,5,7-trimethyl-indan-1-one and 11.3 % dimers (GC). Yield based on GC purity 89%. This product was used without any further purification.

(b) Synthesis of 2,5,7-trimethyl-indan-1-ol 6.13 g of LiAlH$_4$ and 250 mL Et$_2$O were placed in a 3-neck 500 mL round bottomed flask equipped with magnetic stirring bar, reflux condenser and 100 mL dropping funnel. A 100 mL solution of 26.13 g of the product obtained at point (a) in Et2O was placed in the dropping funnel and added dropwise at room temperature over 40' in the stirred LiAlH$_4$/Et$_2$O slurry. At the end of the addition, the slurry was refluxed for two hours, then cooled with an ice water bath. Subsequently, 5 mL of H$_2$O, 5 mL of a 10% NaOH solution and again 5 mL of H$_2$O were slowly added, the slurry was filtered and the filtrate dried over Na$_2$SO$_4$, filtered and evaporated on the rotavac to leave 25.28 g of a yellow oil which solidifies upon cooling. GC analysis shows the presence of the two diastereomers of 2,5,7-trimethyl-indan-1-ol.

(c) Synthesis of 2,4,6-trimethyl-indene 25.03 g of the product, obtained at point (b) 75 mg of p-toluen-sulfonic acid and 150 mL of toluene were placed in a 250 mL round bottomed flask equipped with magnetic stirring bar. The solution was heated at 80° C. for 15', then treated with a saturated NaHCO$_3$ aqueous solution and the organic layer separated, washed with water, dried over Na$_2$SO$_4$ and evaporated in vacuo to leave 23.35 g of an orange oil. GC analysis: 2,4,6-trimethylindene 86.9%. This product was used in the next step without any further purification.

(d) Synthesis of bis(2,4,6-trimethyl-indenyl) zirconium dichloride

A solution of 4.0 g of 2,4,6-trimethylindene obtained at point (c) in 20 ml THF was added dropwise to a suspension of 0.98 g KH in 80 ml THF at room temperature. H$_2$ evolution was observed. At the end of the addition the mixture was stirred until gas evolution ceased (2 hours). The remaining solid was decanted off and the dark brown liquid was transferred into a 100 ml dropping funnel and added dropwise into a flask containing a rapidly stirring solution of 4.14 g of ZrCl$_4$(THF)$_2$ in 50 ml THF. During the addition a brown-yellow suspension was obtained. After stirring at room temperature for 2 hours (yellow suspension) the volume of the slurry was concentrated to 10 ml and 20 mL of Et$_2$O was added. The mixture was stirred for a few minutes and filtered. The filtrate was cooled to −20° C., and 0.825 g of solid precipitated and were isolated by filtration (A). The yellow solid was washed with 5 mL HCl 4N, 5 mL H$_2$O, 5 mL EtOH and 2×5 mL Et$_2$O. After drying, 1.854 g of bright yellow solid were obtained (B). The two solid fractions (A) and (B) were combined and continuously extracted with CH$_2$Cl$_2$ (80 mL, 4 hours), then dried, yielding 1.874 g of (2,4,6-trimethyl-indenyl)$_2$ZrCl$_2$ (pure by $^1$H NMR, 1:1 mixture of its two isomers).

EXAMPLE 6
(Comparison)

Bis(4,6-dimethyl-indenyl)zirconium Dichloride (a) Synthesis of 5,7-dimethyl-indan-1-one 150 mL of CH$_2$Cl$_2$ and 72 g of AlCl$_3$ (Aldrich) were placed in a 500 mL, 3-neck round bottomed flask equipped with magnetic stirring bar, 250 mL dropping funnel, thermometer and reflux condenser. The flask was placed in a Dewar and cooled to 0° C. A solution of 21 mL of acryloyl chloride (Aldrich, 98%) and 31 mL of m-xylene (Aldrich) in 100 mL of CH$_2$Cl$_2$ was placed in the dropping funnel and added dropwise to the stirred AlCl$_3$/CH$_2$Cl$_2$ slurry over 2 hours (hexothermic reaction with HCl evolution). A red-orange slurry was obtained, which was allowed to warm to room temperature and stirred overnight (18 hours). The slurry was then slowly poured into a flask containing 200 mL of 37% HCl and 200 g of ice. The solids were decanted off, the organic layer separated, the aqueous layer extracted three times with Et$_2$O. The combined organic layers were washed with a saturated aqueous solution of NaHCO$_3$ and then water, dried over Na$_2$SO$_4$, filtered and evaporated on the rotavac to leave 41.06 g of an oil, containing 58.65% 5,7-dimethyl-indan-1-one identified by GC. Yield 60%. This product was used in the next step without any further purification.

(b) Synthesis of 5,7-dimethyl-indan-1-ol 5.1 g of LiAlH$_4$ and 250 mL Et$_2$O were placed in a 3-neck 2-L round bottomed flask equipped with magnetic stirring bar, reflux condenser and 250 mL dropping funnel. A 250 mL solution of 41 g of the product obtained at point (a) in Et$_2$O was placed in the dropping funnel and added dropwise at room temperature over 80' in the stirred LiAlH$_4$/Et$_2$O slurry. At the end of the addition, the slurry was refluxed for two hours, then cooled with an ice water bath. Subsequently, 10 mL of H$_2$O, 10 mL of a 15% NaOH solution and again 10 mL of H$_2$O were slowly added, the slurry was filtered and the filtrate dried over Na$_2$SO$_4$, filtered and evaporated on the rotavac to leave 44.60 g of a yellow oil which solidifies upon cooling. GC analysis confirms the presence of 57% 5,7-dimethyl-indan-1-ol. The product was used in the next step without any further purification.

(c) Synthesis of 4,6-dimethyl-indene 44.036 g of the product obtained at point (b), 350 mg of p-toluen-sulfonic acid and 400 mL of toluene were placed in a 1-L round bottomed flask equipped with magnetic stirring bar and reflux condenser. The solution was heated at 80° C. for 15', then treated with a saturated NaHCO$_3$ aqueous solution and the organic layer separated, washed with water, dried over Na$_2$SO$_4$ and evaporated in vacuo to leave 35.425 g of a yellow-orange oil. 33.86 g of this oil was distilled on a 10 cm Vigreux column (62–63° C., 0.7 mmHg) in the presence of NaOH. 17 ml of a yellow liquid were recovered. GC analysis: 4,6-dimethylindene 95.0%. The product was used in the next step without any further purification.

(d) Synthesis of bis(4,6-dimethyl-indenyl)zirconium dichloride 7.0 g of 4,6-dimethylindene obtained at point (c) in 30 ml THF was added dropwise to a suspension of 2.05 g KH in 90 ml THF at room temperature. H$_2$ evolution was observed. At the end of the addition the mixture was stirred until gas evolution ceased (2 hours). The remaining solid was decanted off and the dark green liquid was transferred into a 250 ml dropping funnel and added dropwise into a flask containing a rapidly stirring solution of 8.69 g of ZrCl$_4$(THF)$_2$ in 80 ml THF. During the addition the solution becomes cloudy orange. After stirring at room temperature for 2 hours (a yellow slurry was formed) the volume of the slurry was concentrated to 10 ml and an equal volume of Et$_2$O was added. The mixture was stirred for a few minutes and filtered. The yellow solid was washed with 10 mL HCl 4N, 10 mL H$_2$O, 5 mL EtOH and Et$_2$O (5×2+12×2 mL) and finally dried, yielding 6.72 g of a yellow solid identified as bis(4,6-dimethyl-indenyl)zirconium dichloride by $^1$H-NMR analys.

EXAMPLE 7
(Comparison)

Bis(2-t-butyl-indenyl)zirconium Dichloride (a) Preparation of 2-isopropylidene-1-indanone To a solution of 1-indanone (120 g, 0.908 mole) in acetone (180 g) inside of 500 mL round-bottom flask was added 9 mL of ethanolic potassium hydroxide (3 g, 0.054 mole) solution. The solution was heated under reflux for 7.5 hours and then acidified with acetic acid. Volatile components were removed by a rotary evaporator. To the residue diethyl ether (200 mL) and water (100 mL) were added. The aqueous layer was extracted with diethyl ether (4*200 mL). All etheral layers were combined, washed with water (50 mL), dried over anhydrous magnesium sulfate and concentrated to yield 152 g of crude product. Fractional distillation (80 to 120° C./0.3 mmHg) and recrystallization from methanol yielded 29 g of 2-isopropylidene-1-indanone. H-NMR (CDCl$_3$) δ 1.99 (s, 3 H), 2.43 (s, 3 H), 3.62 (s, 2 H), 7.36 (br t, J=7.6 Hz, 1 H), 7.45 (br d, J=7.6 Hz, 1 H), 7.53 (td, J=7.6, 1.2 Hz, 1H), 7.80 (br d, J=7.6 Hz, 1H).

(b) Preparation of 2-t-butyl-1-indanone

To the cupurous chloride (0.258 g, 2.61 mmol) inside 250 mL round bottom flask was added 22 mL of methylmagnesium iodide (3.0 M solution in diethyl ether, 66 mmol) at 0° C. under nitrogen. Diethyl ether was removed in vacuo. Tetrahydrofuran (65 mL) was then introduced. To this resulting suspension was added a solution of 2-isopropylidene-1-indanone (5.00 g, 29 mmol) in Tetrahydrofuran (25 mL) through a dropping funnel dropwise at 0° C. The mixture was stirred at the same temperature for another 1 h and then at ambient temperature overnight (16 h). The slurry was poured into ice (32 g) containing ammonium chloride (6.44 g). The solution was extracted with diethyl ether (5*80 mL). All ethereal layers were combined, washed with water (20 mL), dried over anhydrous magnesium sulfate and concentrated to yield 5.29 g (97%) of 2-t-butyl-1-indanone. H-NMR (CDCL$_3$) δ 0.95 (s, 9H), 2.38 (dd, J=4.3, 8.0 Hz, 1 H), 2.90 (dd, J=4.3, 17.4 Hz, 1H), 3.08 (dd, J=8.0, 17.4 Hz, 1H) 7.23 (br t, J=7.4 Hz, 1H), 7.35 (br d, J=7.6 Hz, 1H), 7.46 (br t, J=7.6 Hz, 1H), 7.61 (br d, J=7.4 Hz, 1H):

(c) Preparation of 2-t-butyl-1-indanol

To a suspension of lithium aluminium hydride (1.164 g, 30.7 mmol) in anhydrous diethyl ether (100 mL) was added a solution of 2-t-butyl-1-indanone (8.32 g, 49.6 mmol) in anhydrous diethyl ether (100 mL) under nitrogen. The mixture was stirred at ambient temperature overnight (16 h). Water (1.2 mL), 15% aqueous sodium hydroxide (1.2 mL), water (3.5 mL) were added consequently. Solid was filtered off and washed with ether (200 mL). Etheral solution was dried over anhydrous magnesium sulfate and concentrated to yield 8.19 g (87%) of 1:1 mixture of diastereomers of 2-t-butyl-1-indanol. $^1$H-NMR (CDCL$_3$) δ 1.02(s), 1.16 (s, overlapping a broad singlet at 1.16, total 10 H), 1.96–2.10 (m, 1H), 2.64–2.84 (m, 1H), 2.95–3.10 (m, 1H), 5.00–5.15 (m, 1H), 7.16–7.28 (m, 3 H), 7.35–7.40 (m, 1H).

(d) Preparation of 2-t-butyl-indene

A solution of 2-t-butyl-1-indanol (8.19 g, 43.1 mmol) and p-toluenesulfonic acid (0.200 g, 1.05 mmol) in benzene was heated under reflux for 0.5 h. Water (20 mL) was added. Aqueous layer was extracted with ether (4*50 mL). All organic layers were combined, washed with water (20 mL), brine (10 mL) and concentrated to produce 7.41 g (100 g) of 2-t-butyl-indene. $^1$H-NMR (CDCl$_3$) δ 1.18 (s, 9 H), 3.30 (s, 2H), 6.45 (s, 1H), 7.02 (tdd, J=7.3, 1.4, 0.3 Hz, 1H), 7.14 (br t, J=7.5 Hz, 1H), 7.19 (br d, J=7.3 Hz, 1H), 7.31 (br d, J=7.3 Hz, 1 H). $^{13}$C-NMR (CDCl$_3$) δ 30.44, 33.45, 37.84, 120.09, 123.42, 123.50, 123.63, 126.25, 143.11, 145.49, 150.16.

(e) Synthesis of 2-t-butyl-indenyl-zirconium dichloride 3.13 g of 2-t-butyl-indene in 50 mL THF were added dropwise to 0.81 g of KH in 170 mL THF. At the end of the addition the suspension was stirred for 2 hours at room temperature. Excess KH was decanted off and the yellow-green solution was added dropwise (3 h) to a solution of 3.42 g of ZrCl$_4$(THF)$_2$ in 70 mL THF. The yellow suspension was stirred for additional 18 hours, then concentrated in vacuo to a volume of approximately 10 mL, and 40 mL of Et$_2$O were added. The slurry was stirred for a few minutes, then filtered, and the solid was washed with Et$_2$O until the washing was colourless. A white solid, soluble in water, was left on the frit, and was discarded. All ethereal fractions were combined and dried in vacuo, to give a sticky solid which was washed with hexane until a lemon-yellow, free flowing powder was obtained, which was dried in vacuo (1.63 g). This product was (2-t-butyl-indenyl)$_2$ZrCl$_2$ pure by $^1$H-NMR. Yield 36%.

$^1$H-NMR (δ, ppm, CDCl$_3$): 7.7–7.8 (m, 4H), 7.2–7.3 (m, 4H), 5.85 (s, 4H) and 1.0 (s, 18H).

EXAMPLE 8

Bis(2-methyl-4,5,6,7-tetrahydroindenyl)zirconium Dichloride 0.768 g of the bis(2-methyl-indenyl)zirconium dichloride obtained in Example 1 and 45 ml CH$_2$Cl$_2$ were charged in a 50 ml test-tube. The mixture was kept under stirring for 5 minutes at room temperature and to the obtained yellow suspension 25 mg of PtO$_2$ were added. The resulting suspension was then transferred into a 100 ml autoclave. After substitution of the nitrogen atmosphere with an hydrogen atmosphere and rising the pressure to 5 atm. The system was left under stirring for 4 hours at room temperature. At the end of the reaction the catalyst was removed by filtration. The filtrate was concentred until complete removal of the solvent, thus obtaining 0.603 g of a white solid identified as bis(2-methyl-4,5,6,7-tetrahydroindenyl)zirconium dichloride by $^1$H-N.M.R. analysis.

Polymerization of Propylene
Methylalumoxane (MAO)

A commercial (Schering, MW 1400) 30% toluene solution of MAO was used. After having removed the volatile fractions under vacuo, a solid glassy material was finely crushed and further treated in vacuo (0.1 mmHg) for 4–6 hours, at a temperature perature of 40–50° C. to leave a white powder.
Modified Methylalumoxane (M-MAO)

The commmercial (Ethyl) isopar C solution (62 g Al/L) was used as received.

EXAMPLES 9–10

A 1.4 l steel autoclave equipped with a magnetic stirrer manometer, temperature indicator, a 35 ml barrel for loading the catalyst, a feed line for the monomers, a forced circulation thermostating jacket, and a control for the synthesis conditions by means of an automatic computerised system was used.

Into the autoclave, which had been previously washed with gaseous propylene at about 70° C., and brought to the reaction temperature indicated in Table 1, 1.0 l of liquid propylene was loaded.

The catalyst solution was prepared by pre-contacting the amounts of MAO and bis(2-methyl-indenyl)zirconium dichloride indicated in Table 1 in 10 ml of toluene, for 10 minutes at room temperature.

The catalyst solution was fed into the autoclave through the barrel under pressure of pure nitrogen. After the reaction time indicated in Table 1 at a constant temperature, the non-reacted monomer was degassed and the product so obtained was dried under nitrogen in an oven under vacuo at 60° C.

The polymerization conditions and the characterisation data of the obtained polymer are reported in Table 1. From DSC analysis no peaks were observed attributable to the melt enthalpy.

EXAMPLES 11–14

These were carried out according to the procedure described in the examples 9–10, but using a 1.0 l steel autoclave equipped with a magnetic stirrer, manometer, temperature indicator, a barrel for loading the catalyst, a feed line for the monomers and a forced circulation thermostating jacket, and loading 0.4 l of liquid propylene.

The polymerization conditions and the characterization data of the polymers obtained are reported in table 1. From DSC analysis, no peaks were observed attributable to the melt enthalpy.

EXAMPLES 15–18

These were carried out according to the procedure described in the examples 9–10, but using a 1.0 l glass autoclave equipped with a magnetic stirrer, manometer, temperature indicator, a barrel for loading the catalyst, a feed line for the monomers and a forced circulation thermostating jacket, and loading 0.4 l of liquid propylene.

The polymerization conditions and the characterizing data of the polymers obtained are reported in table 1. From DSC analysis, no peaks were observed attributable to the melt enthalpy.

EXAMPLE 19

(Comparison)

This was carried out according to the procedure described in the examples 9–10, but using bis(indenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLES 20–22

(Comparison)

These were carried out according to the procedure described in the examples 11–14, but using bis(indenyl)zirconium dichloride instead of bis(2-methyl-indenyl)zirconium dichloride.

The polymerization conditions and the characterizing data of the polymers obtained are reported in table 1. From DSC analysis, no peaks were observed attributable to the melt enthalpy.

EXAMPLE 23

This was carried out according to the procedure described in the examples 9–10, but using bis(2,4,7-trimethyl-indenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLES 24

(Comparison)

This was carried out according to the procedure described in the examples 9–10, but using bis(4,7-dimethyl-indenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLE 25

This was carried out according to the procedure described in the examples 9–10, but using bis(2,4,6-trimethyl-indenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLES 26

(Comparison)

This was carried out according to the procedure described in the examples 9–10, but using bis(4,6-dimethyl-indenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLES 27

This was carried out according to the procedure described in the examples 11–14, but using bis(2-methyl-4,5,6,7-tetrahydroindenyl)zirconium dichloride instead of bis(2-methyl-indenyl)zirconium dichloride.

The polymerization conditions and the characterizing data of the polymer obtained are reported in table 1. From DSC analysis, no peaks were observed attributable to the melt enthalpy.

EXAMPLES 28

(Comparison)

This was carried out according to the procedure described in the examples 11–14, with the exception that the catalyst solution was prepared by pre-contacting, for 10 minutes at room temperature, 2.58 ml of M-MAO solution in isopar C (5.94 mmoles Al) with 1 mg of bis(2-t-butyl-indenyl)zirconium dichloride in 1 ml of toluene. No polymer was obtained.

The polymerization conditions are reported in table 1.

EXAMPLES 29

(Comparison)

It was worked according to the procedure described in example 28, but using 10 mg of bis(2-t-butyl-indenyl)zirconium dichloride in 5 ml of toluene. No polymer was obtained.

The polymerization conditions are reported in table 1.

TABLE 1

| EXAMPLE | metallocene | Zr (μmoles) | Al/Zr (mol) | T (°C.) | time (min) | yield (grams) | activity (Kg$_{pol}$/mmol$_{Zr}$h) | I.V. (dL/g) | m-r (%) | B |
|---|---|---|---|---|---|---|---|---|---|---|
| 9 | (2-Me-Ind)$_2$ZrCl$_2$ | 8.8 | 1000 | 50 | 60 | 57 | 6.5 | 0.26 | 7.72 | 0.98 |
| 10 | " | 8.8 | 1000 | 30 | 60 | 51 | 5.8 | 1.58 | 18.28 | 1.11 |
| 11 | " | 2.4 | 3000 | 30 | 60 | 9.5 | 4.0 | 1.45 | n.a. | n.a. |
| 12 | " | 2.4 | 3000 | 25 | 60 | 10.8 | 4.5 | 2.72 | n.a. | n.a. |
| 13 | " | 2.4 | 3000 | 20 | 15 | 9.2 | 15.0 | 4.18 | 19.60 | 1.13 |
| 14 | " | 2.4 | 3000 | 10 | 60 | 17.6 | 7.3 | 6.46 | 21.51 | 1.21 |
| 15 | " | 7.6 | 1000 | 0 | 60 | 61.4 | 8.0 | 11.43 | 17.60 | 1.28 |
| 16 | " | 1.2 | 3000 | 0 | 60 | 11.5 | 9.6 | 11.23 | n.a. | n.a. |
| 17 | " | 3.6 | 1000 | −10 | 20 | 10.9 | 9.1 | 11.55 | 23.30 | 1.15 |
| 18 | " | 1.8 | 2000 | −20 | 25 | 5.9 | 7.9 | 13.24 | 24.30 | 1.09 |
| 19 COMP. | (Ind)$_2$ZrCl$_2$ | 15.3 | 1000 | 50 | 120 | 278 | 9.0 | liquid | n.a. | n.a. |
| 20 COMP. | " | 5.8 | 1400 | 50 | 60 | 105 | 18.0 | liquid | 8.4 | 8.4 |
| 21 COMP. | " | 2.5 | 3000 | 20 | 60 | 11.9 | 4.7 | 0.63 | 7.93 | 1.01 |
| 22 COMP. | " | 2.5 | 3000 | 0 | 60 | 4.7 | 1.8 | 1.82 | 11.9 | 0.9 |
| 23 | (2,4,7-Me$_3$-Ind)$_2$ZrCl$_2$ | 8.4 | 1000 | 50 | 60 | 33 | 3.9 | liquid | 29.28 | 1.07 |
| 24 COMP. | (4,7-Me$_2$-Ind)$_2$ZrCl$_2$ | 8.9 | 1000 | 50 | 120 | 3.5 | 0.2 | liquid | n.a. | n.a. |
| 25 | (2,4,6-Me$_3$-Ind)$_2$ZrCl$_2$ | 8.4 | 3000 | 50 | 60 | 27.6 | 3.3 | 0.15 | 15.68 | 1.03 |
| 26 COMP. | (4,6-Me$_2$-Ind)$_2$ZrCl$_2$ | 8.9 | 3000 | 50 | 60 | 3.9 | 0.4 | 0.19 | 14.94 | 1.98 |
| 27 | (2-Me-H$_4$Ind)$_2$ZrCl$_2$ | 9.8 | 1000 | 20 | 60 | 8.65 | 0.9 | 0.68 | 2.80 | 0.90 |
| 28 COMP. | (2-tBu-Ind)$_2$ZrCl$_2$ | 2.0 | 3000 | 50 | 60 | 0 | — | — | — | — |
| 29 COMP. | " | 20.0 | 300 | 70 | 60 | 0 | — | — | — | — | n.a. = not available

What is claimed is:

1. A process for the preparation of substantially amorphous polymers of propylene having melting enthalpies ($\Delta H_f$) that are not measurable by differential scanning calorimetry, said process comprising polymerizing propylene and optionally one or more olefins to obtain a homopolymer of propylene or a copolymer of propylene with at least 90% by mole of propylene units, said polymerization being carried out in the presence of a catalyst comprising the product of the reaction between:

(A) a metallocene compound selected from the group consisting of bis-indenyl compounds of formula (I):

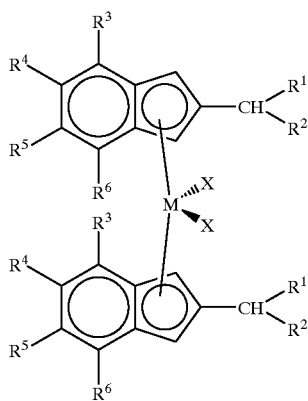

(I)

and the corresponding bis-4,5,6,7-tetrahydroindenyl compounds, wherein:

on each indenyl or tetrahydroindenyl group the substituents $R^1$ and $R^2$, same or different from each other, are hydrogen atoms, —CHR$_2$ groups, or —CHR— groups that form a cycle comprising from 3 to 8 carbon atoms, wherein the R substituents are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals or $C_7$–$C_{20}$ aralkyl radicals and can contain Si or Ge atoms; the substituents $R^3$, $R^4$, $R^5$ and $R^6$, same or different from each other, are defined as R substituents, in addition two adjacent $R^3$, $R^4$, $R^5$ and $R^6$ substituents on the same ring can form a ring comprising from 5 to 8 carbon atoms; M is a transition metal atom of groups IVb, Vb or VIb of the Periodic Table; substituents X, same or different from each other, are hydrogen atoms, halogen atoms, —R$^7$, —OR$^7$, —SR$^7$, —NR$^7_2$ or —PR$^7_2$ groups where substituent R$^7$ are defined as substituent R; and (B) at least a compound selected from the group consisting of (a) organo-metallic compounds of aluminum containing at least a heteroatom selected from the group consisting of oxygen, nitrogen and sulphur, and (b) compounds capable of reacting with the metallocene compound to form an alkyl metallocene cation.

2. The process according to claim 1, wherein the metallocene compound of formula (I) is present as the reaction product with an organometallic compound of aluminium of formula AlR$^8_3$ or Al$_2$R$^8_6$, where substituents R$^8$, same or different, are defined as substituent R or are halogen atoms.

3. The process according to claim 1 wherein, in each of the two indenyl or tetrahydroindenyl groups of the metallocene compound of formula (I), the substituents $R^3$ are the same as substituent $R^6$, while the substituents $R^4$ are the same as substituent $R^5$.

4. The process according to claim 2, wherein in the metallocene compound of formula (I) the substituents $R^3$, $R^4$, $R^5$ and $R^6$ are hydrogen atoms.

5. The process according to claim 1, wherein in the metallocene compound of formula (I) the transition metal M is selected from the group consisting of Ti, Zr and Hf.

6. The process according to claim 1, wherein in the metallocene compound of formula (I) the substituents X are chlorine atoms or methyl radicals.

7. The process according to claim 1, wherein in the metallocene compound of formula (I) the substituents $R^1$ are $C_1$–$C_3$ alkyl radicals.

8. The process according to claim 7, wherein the substituents $R^1$ are methyl radicals.

9. The process according to claim 1, wherein the organometallic compound of aluminum containing at least a heteroatom is an alumoxane.

10. The process according to claim 1, wherein the alumoxane is present as the reaction product with an organometallic compound of aluminum of formula $AlR^8_3$ or $Al_2R^8_6$, in which substituents $R^8$, same or different from each other, are defined as substituents R or are halogen atoms.

11. The process according to claim 9, in which the alumoxane is methylalumoxane (MAO).

12. The process according to claim 1, wherein the molar ratio between the aluminum and the metal of the metallocene compound is from 10:1 to 10000:1.

13. The process according to claim 1, wherein the polymerization reaction of propylene is carried out in the presence of one or more olefins selected from the group consisting of ethylene and α-olefins containing from 4 to 20 carbon atoms.

* * * * *